United States Patent [19]

Baugh et al.

[11] Patent Number: 4,871,677
[45] Date of Patent: Oct. 3, 1989

[54] METHOD OF COLLECTING AND ANALYZING A SAMPLE OF BLOOD WHEN MONITORING HEPARIN THERAPY

[75] Inventors: Robert F. Baugh, Aurora; Cynthia A. Taylor, Denver, both of Colo.

[73] Assignee: Hemotec, Inc., Englewood, Colo.

[21] Appl. No.: 233,207

[22] Filed: Aug. 17, 1988

Related U.S. Application Data

[62] Division of Ser. No. 705,507, Feb. 25, 1985, Pat. No. 4,782,026.

[51] Int. Cl.$^4$ .............................................. G01N 33/86
[52] U.S. Cl. ........................................ 436/69; 435/13; 436/176; 436/18
[58] Field of Search ..................... 436/63, 69, 18, 176; 435/13, 2; 424/101

[56] References Cited

U.S. PATENT DOCUMENTS

| | | | |
|---|---|---|---|
| 4,067,777 | 1/1978 | Innerfield et al. | 435/13 |
| 4,116,635 | 9/1978 | Jaeger | 435/17 |
| 4,243,671 | 1/1981 | Harris et al. | 514/396 |
| 4,359,463 | 11/1982 | Rock | 424/101 |
| 4,540,801 | 9/1985 | Nysted et al. | 544/376 |

Primary Examiner—Robert J. Hill, Jr.
Assistant Examiner—T. J. Wallen
Attorney, Agent, or Firm—John R. Ley; Gary M. Polumbus

[57] ABSTRACT

An inhibitor of platelet-related procoagulant activity is included in a collection medium into which a whole blood sample is collected. The inhibitor prevents an initial drop in the recalcified activated clotting time measured during an assay test conducted on the whole blood sample collected in citrate in the medium. The discovery of the problem of the initial drop in the activated clotting time and the solution of including the inhibitor of the procoagulant activity is of considerable importance in heparin therapy, since the initial drop in the activated clotting time of heparinized blood is substantial. The inhibitor can be included with a calcium chelating agent in the collection medium. Prostacylin and imidazole, which is an inhibitor of platelet thromboxane A2 synthesis, are effective inhibitors of this platelet-related procoagulant activity.

7 Claims, 2 Drawing Sheets

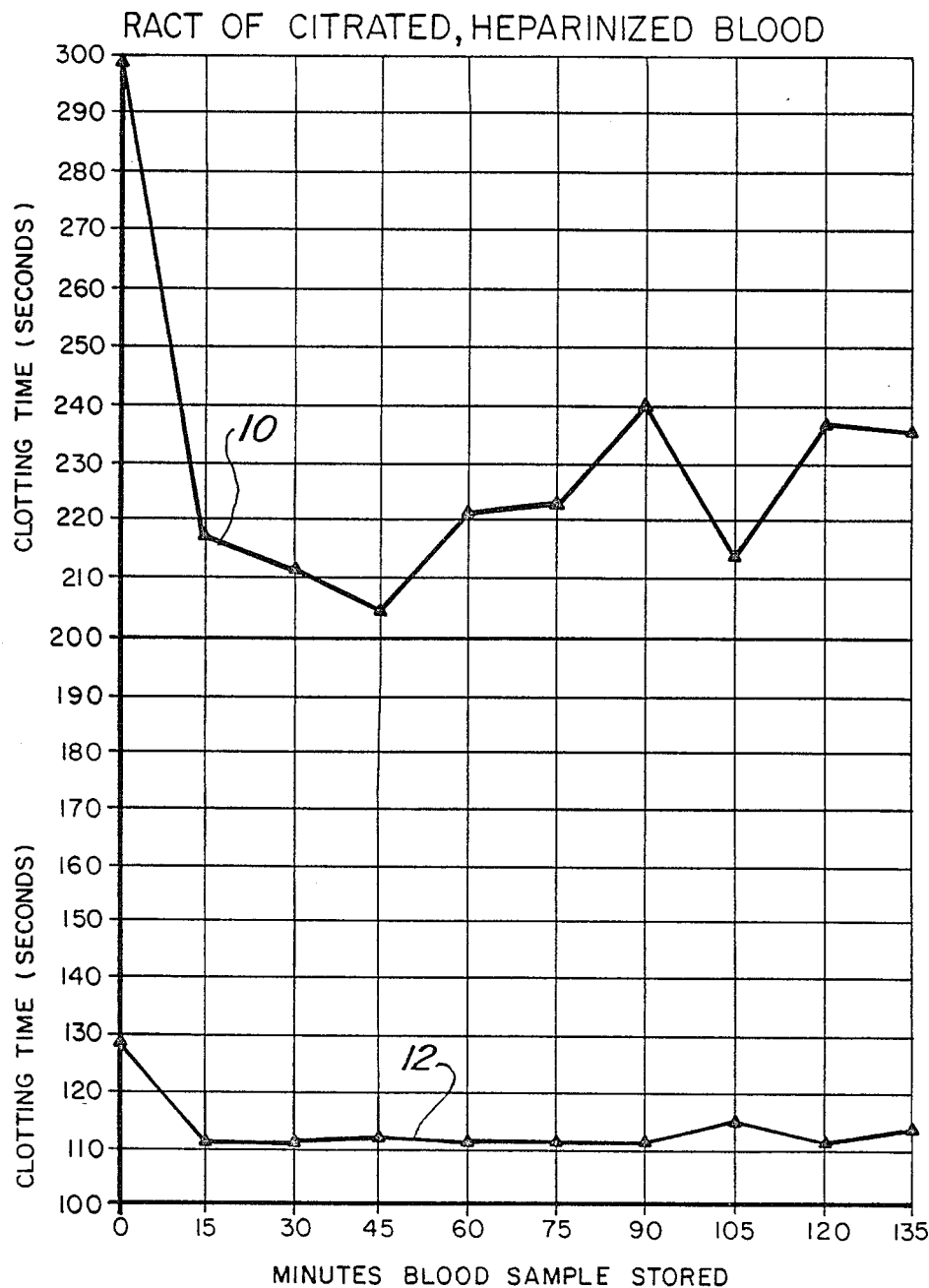
Fig_1

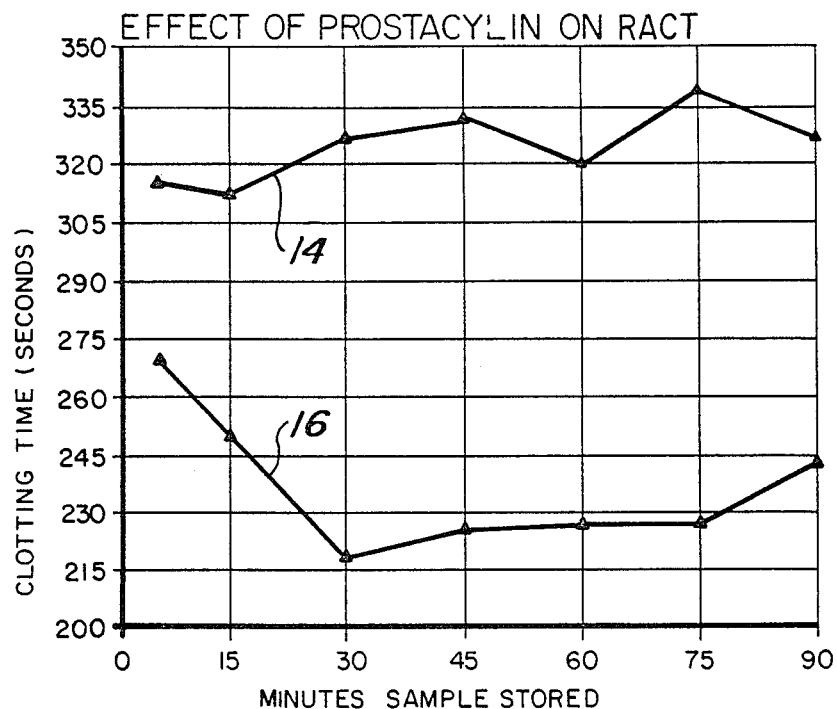
Fig_2
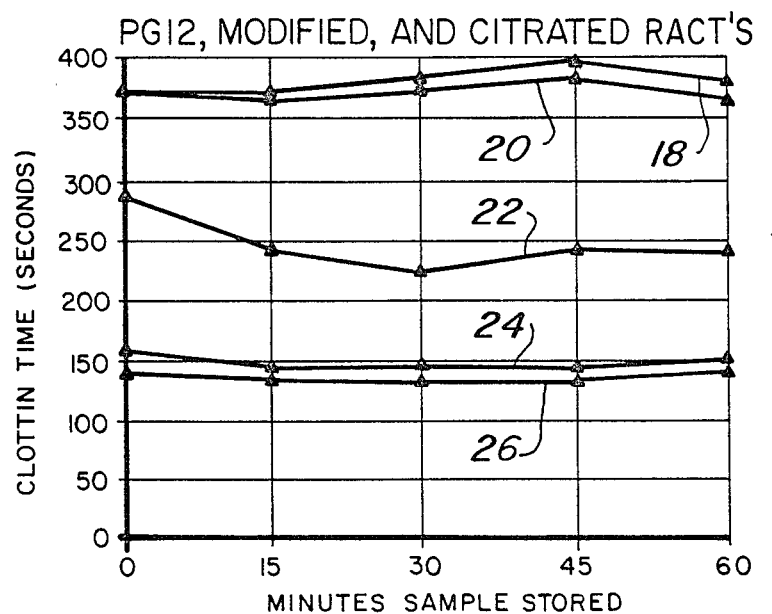
Fig_3
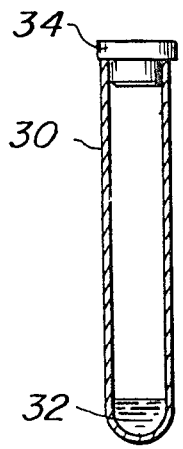
Fig_4

METHOD OF COLLECTING AND ANALYZING A SAMPLE OF BLOOD WHEN MONITORING HEPARIN THERAPY

CROSS-REFERENCE TO RELATED APPLICATION

This is a division of co-pending application Ser. No. 705,507 filed Feb. 25, 1985 now U.S. Pat. No. 4,782,026, which is assigned to the assignee hereof.

FIELD OF THE INVENTION

The present invention relates to a new and improved collection media for whole blood, and a new and improved method of monitoring heparin therapy utilizing improved techniques of whole blood collection. More particularly, the present invention relates to a solution of a previously unrecognized problem of instability in recalcified activated clotting time test results performed on citrated whole blood, particularly heparinized blood.

BACKGROUND OF THIS INVENTION

Coagulation assays form a group of clinical tests with a wide variety of medical uses. Most coagulation assays are performed on plasma, which is the fluid left after the red blood cells, white blood cells, and platelets (cell fragments from a cell type known as megakaryocytes) are removed either by filtration or centrifugation. The process of clot formation is quite complex, and assays performed on plasma eliminate some of the components involved in clot formation. Historically, the simplification of clotting assays performed on plasma was very important because the technology for measuring clotting had not yet developed to a substantial degree, and the understanding of the coagulation process was very limited. At the present time, however, a more advanced understanding of this clotting process in plasma exists. A large number of automated, highly sophisticated instruments designed specifically for use in plasma-based clotting assays have also been developed over the years. Plasma is also much easier to handle and store than whole blood, and the physical properties of plasma are such that coagulation reactions can be measured with a number of different techniques. A disadvantage of assays performed on plasma is that coagulation is influenced by those components of whole blood which have been removed from the plasma. Plasma-based coagulation clotting assays therefore require the addition of substitutes to attempt to compensate for these missing components.

The addition of substitutes for the missing blood components in a plasma-based assay provides reasonably accurate information regarding in vitro coagulation conditions in whole blood. One frequently performed plasma-based clotting assay is a prothrombin time or PT test. The PT test measures the plasma components of the extrinsic clotting system. The extrinsic clotting system can be thought of as the system which causes blood to clot when a person is cut with a knife, i.e. an open wound. The extrinsic clotting system is triggered by a component known as thromboplastin (or tissue factor), which is located in the linings of the vessels and various cell membranes. In a PT test, thromboplastin is added to the plasma to trigger the formation of a clot. Another frequently performed plasma-based clotting assay is an activated partial thromboplastin time or PTT (or APTT) test. The PTT test is intended to measure the conditions of the intrinsic system. The intrinsic system can be thought of as the clotting system which is triggered when a blood vessel is bruised or damaged. Conducting a PTT test on plasma requires the addition of an activating surface (usually supplied by a negatively charged surface such as glass) and a phospholipid source. The phospholipid substitutes for the activity located on the surface of the platelets known as Platelet Factor 3. Platelet Factor 3 is considerably more effective than phospholipid in promoting clot formation in a PTT test, but Platelet Factor 3 is not used in a PTT test. One frequent complaint with a plasma-based clotting assay is that it does not reliably reflect true in vivo coagulation conditions.

Coagulation assays can also be performed on whole blood, but whole blood coagulation assays are very complex in the information they provide. In whole blood, individual variations exist in hematocrits (the number of red blood cells per unit volume), the number and reactivity of the platelets, and the number and reactivity of white blood cells. In vivo coagulation is affected by each of these components as is in vitro coagulation. The contribution of each of these individual components has, however, not been easily discernible from a clotting assay. In contrast to the more extensive technological developments in plasma-based assays, the technology in whole blood clotting assays has progressed more slowly, primarily because of the historically greater favor for plasma-based assays and because the information available from plasma assays was more managable even though less accurate.

The assignee of the present invention has been instrumental in developing technology useful in performing whole blood coagulation assays. Some of that technology is reflected in U.S. Pat. Nos. 4,000,972, 4,074,971, 4,599,219 and others. The invention of U.S. Pat. No. 4,599,219 can be effectively used to aid in monitoring therapeutic heparin. Generally, therapeutic heparin refers to the use of heparin outside of cardiovascular surgery. Heparin is an agent which extends clotting time of whole blood. In vivo heparin therapy is one very important aspect of modern medicine. In many pathological conditions, accurate knowledge of true intrinsic coagulation conditions can be of considerable aid in assisting with proper treatment in the patient. One feature inherent in U.S. Pat. No. 4,599,219 is the ability to run activated clotting time assays on citrated whole blood samples. Activated clotting time information has been used successfully as an aid in monitoring heparin therapy. In a whole blood activated clotting time test, it is the intrinsic clotting system that is the primary avenue of clot formation. Accordingly, plasma-based PTT tests are not as reliable in supplying information for monitoring heparin therapy as are whole blood activated clotting time tests, which include the effects all of the various components of whole blood which effect clotting.

The standard activated clotting time test on whole blood involves drawing a sample of blood and, as rapidly as possible, placing the sample in a tube containing an activating agent (a negatively charged surface). Generally the activating agent is diatomaceous earth. After mixing the whole blood with the activator agent, the tube is incubated at 37° C. and periodically examined for the formation of a clot. This can be done visually in a manual technique, or the examination can be automated. The apparatus disclosed in U.S. Pat. No.

4,599,299 is an automated system which is capable of running an activated clotting time test on a sample of fresh blood immediately after it has been collected, and which is also capable of performing the activated clotting time test later on a sample of citrated whole blood. Citrated whole blood is whole blood collected in a medium containing a calcium chelating agent, such as sodium citrate (citrate). The whole blood is mixed with the citrate or calcium chelating agent when the sample is collected.

Calcium plays a significant role in the analysis of blood clotting. The act of drawing blood initiates clotting reactions, and unless something is done to stop the process, the clotting times have no diagnostic significance. The formation of a clot is a multi-step process and several of these steps require the presence of calcium ions. By removing the calcium ions, as is the effect when the blood is collected in citrate, the blood can be prevented from clotting. To reinitiate the clotforming process, calcium is added back into the whole blood (recalcification). All plasma-based assays are performed on blood which has been collected into a medium containing a calcium chelating agent. A calcium chelating agent is a chemical which reacts with the calcium in such a fashion that the calcium can no longer function in blood coagulation. The most common chelating agent is citric acid, since it has the fewest side effects on the components of the clotting system. By collecting blood into a medium containing a calcium chelating agent such as citric acid, sample collection and the assay on the citrated sample can be separated by a time period of up to six hours. Plasma obtained from citrated whole blood can also be frozen, for example, for shipment to a laboratory which specializes in exotic clotting assays. Obtaining plasma from citrated whole blood provides the convenience of highly automated instruments, batch processing of large numbers of samples, and significant savings in operator skill level, time utilization and cost. However, the added convenience of plasma-based samples eliminates any consideration in assays of whole blood components which participate in intrinsic coagulation.

Most hospitals and laboratories, if they choose to run whole blood clotting assays, would like to be able to use citrated whole blood. The use of citrated whole blood means that the assay does not have to be run at bedside, and allows the assays to be batch-processed. The apparatus disclosed in U.S. Pat. No. 4,599,299 is readily used to perform activated clotting time tests on recalcified samples of whole blood collected initially in citrate or in some other calcium chelating agent, to thereby provide the convenience for delaying the assay from the time when the blood sample was collected.

THE INVENTION

In performing activating clotting time assays on whole blood samples, it was discovered that a marked difference in results occurred between an activated clotting time test run at bedside and a recalcified activated clotting time test or citrated whole blood samples run more than an hour after drawing the blood sample. Laboratory tests were conducted to reproduce the problem and the phenomena. A fresh drawn sample of blood was collected in citrate, heparin was added (to mimic a sample of blood from a patient on heparin therapy), and the recalcified activated clotting time was assayed at various time intervals. FIG. 1 illustrates in Curve 10 an exemplary graph of the recalcified activated clotting time with respect to time, when the sample was stored at 37° C. for periods up to 135 minutes. Initially, the clotting time for one unit of heparin per milliliter of blood resided in the 300 second range (similar to the activated clotting time), but later dropped to the 200 second range. Usually, this initial drop in activated clotting time was complete within 15 to 30 minutes after the sample was drawn. After this initial 15 to 30 minute time period, the activated clotting time stabilized.

This same phenomena of an initial drop in the recalcified activated clotting time also occurred with unheparinized samples of whole blood. However, the magnitude of the initial drop, even in the most severe cases, was only about 10 seconds. Curve 12 of FIG. 1 illustrates the results of a typical recalcified activated clotting time test which occurs with unheparinized blood samples which were collected in citrate and later recalcified for the recalcified activated clotting time tests.

The magnitude of initial drop in the activated clotting time was dependent on the elapsed time after drawing the sample and on the individual subject or patient from whom the blood was drawn. Furthermore, the magnitude of the drop varied with the amount of heparin in the sample, i.e. the greater the initial clotting time, the greater the magnitude of the drop.

The initial drop in the recalcified activated clotting time of heparinized whole blood could cause potentially serious consequences in the monitoring of heparin therapy, since the magnitude of the drop was patient specific and dependant on the heparin concentration. Heparin therapy is monitored by coagulation reactions because clotting times are proportionally related to heparin concentrations. Heparin therapy is intended to generally correlate to the in vivo coagulation conditions, but it appears that significantly different test results could be obtained dependent on the amount of time which lapsed between the time when the blood sample was drawn and the time when the recalcified activated clotting time test was performed. Thus, recalcified activated clotting time tests performed a significant time period after drawing blood would reflect results which would be somewhat inaccurate compared to the actual in vivo situation. The in vivo situation is more closely represented by the activated clotting time test performed at bedside approximately contemporaneously with drawing the blood sample.

In many situations the problem of the initial drop in recalcified activated clotting times might be dealt with by simply recognizing that the problem existed. However, many hospital laboratories are not technically staffed to be able to adequately approach the problem from a recognition-only standpoint. Efforts were therefore directed toward identifying the cause of this problem.

As a result of the discoveries and studies described below, platelets were identified as the cause of this initial drop in the activated clotting time of whole blood. The interaction of platelets with clotting factors has been known for some time, but the nature and extent of the interaction is not totally understood. In the past, it had been thought that Platelet Factor 3 activity was dependant on the phospholipid content of the platelet membrane. During the initiation of coagulation, platelet phospholipid became exposed to those clotting factors which require phospholipid for expressing maximum clotting activity. This concept arose in part from work on the plasma-based partial thromboplastin time test where a number of different phospholipids were used to supply the Platelet Factor 3 requirement for clotting. Studies during the last five years have shown that Platelet Factor 3 is considerably more active in clotting than even the best phospholipid. It now appears that Platelet Factor 3 activity consists not only of a platelet phospholipid, but some other component(s) which imparts high activity to the platelet membrane.

In vivo, platelets circulate without being activated. Activation can be achieved in a number of different ways in vitro, but the exact mechanism in vivo is unknown. One postulate invokes a series of biochemicals known as prostaglandins. The prostaglandins are manufactured by various cell types, and they have a profound effect on platelets. One series of prostaglandins causes platelets to activate and then aggregate, while another series prevents platelets from going through activation and aggregation. The postulate suggests that cells lining blood vessels produce a prostaglandin referred to as prostacyclin or PGI 2. Platelets produce another prostaglandin referred to as thromboxane A2. Prostacyclin prevents platelets from activating or from aggregating and also prevents platelets from making thromboxane A2. Thromboxane A2 causes platelets to activate and aggregate in a concentration dependent fashion. Thus, if platelets are allowed to synthesize thromboxane A2, the level of thromboxane A2 in the platelets will build up to the point where the platelets will activate. If the concentration gets high enough, the platelets will aggregate. Thus, in the body, as long as the cells which line the blood vessels are intact and functioning properly to produce prostacyclin, platelets remain in an unactivated state. But if the cells are damaged and the production of prostacyclin ceases, the platelets begin synthesizing thromboxane A2 which can ultimately lead to platelet activation. The actual mechanism in blood is probably much more complex, but the concept is a useful vehicle to explain the discovered observations relating to the initial substantial decrease or drop in the clotting time of heperinized blood in a recalcified activated clotting time test.

Initial studies examined the effects of platelets on the activated clotting time. Several prostacyclin analogs, i.e. chemicals which have activities similar to prostacyclin, were tested for their ability to influence the activated clotting time. Prostacyclin analogs were initially selected because prostacyclin has a number of different activities, is reportedly quite unstable, and at the current time is relatively expensive. None of the analogs worked well in preventing the drop in the recalcified activated clotting times. Finally, prostacyclin itself was examined with respect to its ability to prevent the initial drop in the recalcified activated clotting time of heparinized blood. Prostacyclin successfully prevented the initial drop in recalcified activated clotting time. Studies have shown that the recalcified activated clotting time of blood collected in citrate supplemented with prostacyclin showed no drop in clotting time over a period of 2 hours when stored at 37° C. Curve 14 shown in FIG. 2 illustrates this effect over a period of 90 minutes. Curve 16 illustrates the typical initial drop in recalcified activated clotting time of the same blood sample collected in a citrate medium not containing prostacyclin. Curve 16 is therefore similar to curve 10 shown in FIG. 1.

Based on subsequent studies, it is now believed that the initial drop in recalcified activated clotting time involves a contribution of platelets to clotting. One possible explanation of the effect is that clotting is a series of kinetically linked reactions. Several of these reactions can be rate limiting, depending on the specific conditions. In an activated clotting time test performed on fresh drawn whole blood, the contribution of platelets is rate limiting. However, in recalcified activated clotting time test performed on citrated whole blood at a significant time after collection of the sample, some component of platelet participation has been activated, possibly because the vessel walls are no longer producing prostacyclin to inhibit platelet activation and production of thromboxane A2. Consequently, the time component of coagulation required to form this activity is not revealed by the recalcified activated clotting time test results because the activity has partially or fully developed. Thus, after approximately the first 30 minutes after drawing the blood sample in citrate, the coagulation component from platelet activity has concluded, and consequently, when the recalcified activated clotting time test is performed, the amount of time for the activation is not included within the results of the activated clotting time test. The recalcified activated clotting times of the citrated blood get shorter and shorter until activation is complete.

BRIEF INVENTION SUMMARY

In general terms, the present invention teaches a solution to the previously unrecognized problem relating to the initial drop in recalcified activated clotting times of citrated whole blood samples, particularly heparinized blood samples which are analyzed during the monitoring of heparin therapy. The solution resides in the discovery that a platelet procoagulant activity commences after drawing the blood sample, even though the blood sample is collected in citrate or some other calcium chelating agent. The solution to the problem involves the inclusion of an inhibitor to the whole blood sample when collected in a citrated medium. At the present time, inhibitors which are known to be effective are prostacyclin and imidazole. The inhibitor should be included along with the citrate in the collection medium into which the fresh drawn sample of blood is collected. The instability of activated clotting time test results, i.e. the initial drop during approximately the first fifteen to thirty minutes, in heparinized blood collected in this type of collection medium is thereby avoided. Monitoring of heparin therapy in accordance with the method of the present invention and other coagulation-related medical effects are beneficially improved.

Other aspects, features and details of the present invention can be more completely understood by reference to the following detailed description of a preferred embodiment, taken in conjunction with the drawings, and from the appended claims.

DRAWING DESCRIPTIONS

FIG. 1 is a graph of recalcified activated clotting time of citrated whole blood vs. the elapsed time period after which the blood sample was drawn. The upper curve (10) of the graph represents the behavior of a sample of whole blood which contains one unit per milliliter of heparin. The bottom curve (12) represents the behavior of the same blood sample not containing heparin. This is a representative graph of the behavior of the blood of one individual, but it is typically representative of the behavior of citrated whole heparinized and unheparinized blood in general.

FIG. 2 is a graph similar to the graph of FIG. 1. The upper curve (14) represents the recalcified activated clotting time of a sample of heparinized blood collected in a citrate collection medium also containing prostacyclin. The bottom curve (16) represents the recalcified activated clotting time of a sample of heparinized blood from the same individual collected in a similar citrate collection medium not containing prostacyclin. This is a representative graph of the behavior of the blood of one individual, but it is typically representative of the behavior of heparinized blood in general to prostacyclin.

FIG. 3 is a graph similar to FIGS. 1 and 2. The curves of the graph of FIG. 3 compare the effects of citrate, citrate supplemented with prostacyclin, and citrate supplemented with imidazole as collection mediums for recalcified activated clotting times of one sample of whole blood. The upper two curves (18, 20) represent the recalcified activated clotting times of heparinized blood collected in a prostacyclin supplemented citrate collection medium (curve 18) and in an imidazole-supplemented citrate collection medium (curve 20). The middle curve (22) represents the recalcified activated clotting time of whole blood collected in a 3.8% citrate collection medium. The lower two curves (24, 26) are baseline curves representing the recalcified activated clotting times of unheparinized whole blood collected into the prostacyclin-and imidazole-supplemented citate collection mediums, respectively.

FIG. 4 shows a test tube with the collection medium of the invention.

PREFERRED EMBODIMENT

Although prostacyclin is effective in preventing the initial drop in recalcified activated clotting times of citrated whole blood, prostacyclin is expensive and it is reported to have a half-life measured in hours. The half-life is that time which is required for initial activity to decay to one half of the previous activity. For commercial embodiments of a collection medium including an inhibitor of the phenomenon, prostacyclin is probably of limited utility due to its relatively high cost and relatively short half-life. Commercial blood collection media will typically be manufactured a substantial number of months in advance of the date of actual use. Nonetheless, in specialized instances, the use of prostacyclin in accordance with the present invention is a viable approach to inhibiting procoagulation activity in samples of blood collected in collection media.

To avoid the cost and instability problems associated with prostacyclin, it was discovered that inhibitors of platelet thromboxane A2 synthesis prevent the observed Platelet Factor 3 activation. Imidazole is an inhibitor of thromboxane A2 synthesis, and is also a relatively common, inexpensive and stable buffering agent in many biological studies. Imidazole was included with citrate in a collection medium and was studied. Imidazole was found to prevent the initial drop in the recalcified activated clotting times of heparinized blood. FIG. 3 presents Curves 18 and 20 which compare the results of a recalcified activated clotting time measured on citrated whole blood collected in a 3.8% sodium citrate collection medium or 3.8 mg of sodium citrate per 100 ml of water. A 3.8% sodium citrate collection medium is that which is frequently used to collect and preserve blood for clotting assays. Curve 18 illustrates the effects of including prostacyclin in the 3.8% sodium citrate collection medium at a concentration of 10 nanograms per milliliter of blood collected. Curve 20 illustrates the effects of including imidazole at a 50 mM concentration in the 3.8% sodium citrate collection medium. Note that neither the prostacyclin-supplemented nor the imidazole-supplemented 3.8% sodium citrate collection medium resulted in any significant decline in the recalcified activated clotting times of heparinized whole blood after collection. Thus both were effective in preventing the initial drop in the recalcified activated clotting times of citrated heparinized whole blood. However, Curve 22 illustrates that the decline does in fact occur with the same blood sample collected in only a 3.8% sodium citrate collection medium, very similarly to that initial drop which has been illustrated by Curve 10 in FIG. 1 and Curve 16 in FIG. 2. Curves 24 and 26 shown in FIG. 3 illustrate the effects of prostacyclin and imidazole, respectively, on the activated clotting times of unheparinized blood samples collected in 3.8% sodium citrate collection medium. Comparison of Curves 18 and 20 reveals that the effects of prostacyclin and imidazole in the collection medium are very comparable.

It was also discovered that the whole blood sample should be collected into the collection medium which previously contained the 50 mM concentration of imidazole and the 3.8% sodium citrate. The desired amount of imidazole could not be added to the blood sample a significant amount of time after the sample was collected. It does appear possible that the imidazole could be added immediately after the sample was collected, but it is preferable to include the imidazole as a part of the collection medium.

The presently preferred embodiment of a collection medium used in the method of the present invention is illustrated in FIG. 4. A borosilicate glass container 30, such as a test tube, is provided into which approximately 0.5 ml of the collection medium 32 is inserted. The collection medium will preferably contain 10.125 grams of imidazole per 100 milliliters of 3.8% sodium citrate. The collection medium 32 will be sealed inside the container 30 by a non-reactive elastomer stopper 34. Prior to sealing the container 30 with the stopper 34, the interior of the container 30 will be evacuated. After sealing the interior of the container with the stopper 34, the interior of the collection container will be sterilized. A suitable label (not shown) can be attached to the exterior of the container 30 to indicate that the container is to be used for whole blood coagulation assays. The container 30 will be used in the usual fashion to receive a sample of blood drawn from a patient.

The present invention has thus identified a problem of instability (the initial drop) in the recalcified activated clotting times conducted on citrated heparinized (patient) whole blood, discovered a cause of and a solution to the problem (although the exact mechanism of the cause is not fully understood), and has embodied the solution in useful technology including the collection medium described. The invention has a direct and immediate application to monitoring heparinization and heparin therapy by procedures which result in better correlation between coagulation symptoms and assay test results. Practice of the present invention leads to more efficient utilization of time in the hospital setting, provides flexibility for adapting whole blood assay tests to more efficient procedures, results in less processing and handling of the sample, and more efficient use of time in the laboratory setting.

The problem, cause, solution, and preferred application of the present invention have been described with a degree of particularity now known and substantially believed to be accurate. The invention itself is defined by the scope of the appended claims.

The invention claimed is:

1. A method of collecting and analyzing a sample of blood when monitoring heparin therapy, comprising the steps of:

drawing a sample of blood from the patient;

collecting the sample as it is drawn in a collection medium which includes a calcium chelating agent;

mixing an inhibitor with the blood sample approximately simultaneously with collection of the sample, the inhibitor being effective to inhibit a platelet-related procoagulant activity which otherwise normally occurs and substantially concludes within approximately thirty minutes after drawing the blood sample from the patient; and thereafter performing a recalcified activated clotting time test on the blood sample to obtain data useful in monitoring the amount of heparin to be administered.

2. A method as defined in claim 1, wherein the recalcified activated clotting time test is performed more than thirty minutes after the sample of blood was drawn.

3. A method as defined in claim 1 wherein the inhibitor is one of the group consisting of a prostaglandin or an inhibitor of thromboxane A2 synthesis.

4. A method as defined in claim 3 wherein the inhibitor is a prostaglandin and the prostaglandin is a prostacyclin.

5. A method as defined in claim 4 wherein:

the prostacyclin is present in the collection medium in an approximate concentration of 10 nanograms per milliliter of blood to be collected, and the calcium chelating agent is sodium citrate present in the collection medium in an approximate concentration of 3.8% mg per 100 ml of water.

6. A method as defined in claim 3 wherein the inhibitor is an inhibitor of thromboxane A2 synthesis and said inhibitor is imidazole.

7. A method as defined in claim 6 wherein:

the imidazole is present in the collection medium in the approximate concentration of 50 mM, and the calcium chelating agent is sodium citrate present in the collection medium in an approximate concentration of 3.8% mg per 100 ml of water.

* * * * *